United States Patent [19]

Derrieu et al.

[11] Patent Number: 5,527,783
[45] Date of Patent: Jun. 18, 1996

[54] DRY AND POROUS GALENIC FORM BASED ON PLANTS, ITS METHOD OF PREPARATION AND ITS APPLICATIONS

[75] Inventors: Guy Derrieu; Bernard Raynier, both of Cagnes Sur Mer, France

[73] Assignee: Laboratoires Ardeval, Ivry Sur Seine Cedex, France

[21] Appl. No.: 231,997

[22] Filed: Apr. 21, 1994

Related U.S. Application Data

[63] Continuation of Ser. No. 990,990, Dec. 16, 1992, abandoned.

[30] Foreign Application Priority Data

Dec. 23, 1991 [FR] France .................................. 91 15983

[51] Int. Cl.⁶ ...................... A61K 31/715; A61K 31/705; A61K 35/78
[52] U.S. Cl. .................. 514/54; 514/26; 514/58; 514/783; 514/946; 514/951; 536/5; 536/103; 424/195.1
[58] Field of Search .......................... 424/195.1; 514/26, 514/54, 58, 783, 946, 951; 536/5, 103

[56] References Cited

FOREIGN PATENT DOCUMENTS

| | | | |
|---|---|---|---|
| 397447 | 11/1990 | European Pat. Off. ....... | A61K 37/30 |
| 420729 | 4/1991 | European Pat. Off. ....... | A61K 35/78 |
| 549420 | 6/1993 | European Pat. Off. . | |
| 3443242 | 5/1986 | Germany ...................... | A61K 31/70 |

Primary Examiner—Douglas W. Robinson
Assistant Examiner—Howard C. Lee
Attorney, Agent, or Firm—Bell, Seltzer, Park & Gibson

[57] ABSTRACT

Solid compositions based on plants, capable of being converted to a dry and porous galenic form (lyophilized or equivalent form) which is undivided or powdered. Said dry and porous galenic form comprises a solid composition II consisting of a solid composition I composed of:

(A) one or more of the plants' active principles included in a homogeneous suspension of fresh or dry plants obtained by (a) cleaning and/or drying of the plant or part of the plant, (b) cryocomminution at a temperature below 0° C. until a particle size of less than about 100 µm is obtained, (c) immersion of the particles for a suitable time in at least one appropriate solvent, (d) separation of the liquid phase and the solid phase of the suspension obtained, (e) expression of the solid phase obtained in (d) by cold pressing, and (f) mixing of the liquid phase obtained in (d) and the expressed liquid obtained in (e), and (B) at least one absorption promoter with a sequestering action, said mixture (A+B) being dried by removal of the solvent; and (C) at least one absorption promoter selected from surfactants, said composition II being lyophilized and optionally associated with excipients which are suitable from a pharmaceutical point of view.

15 Claims, 2 Drawing Sheets

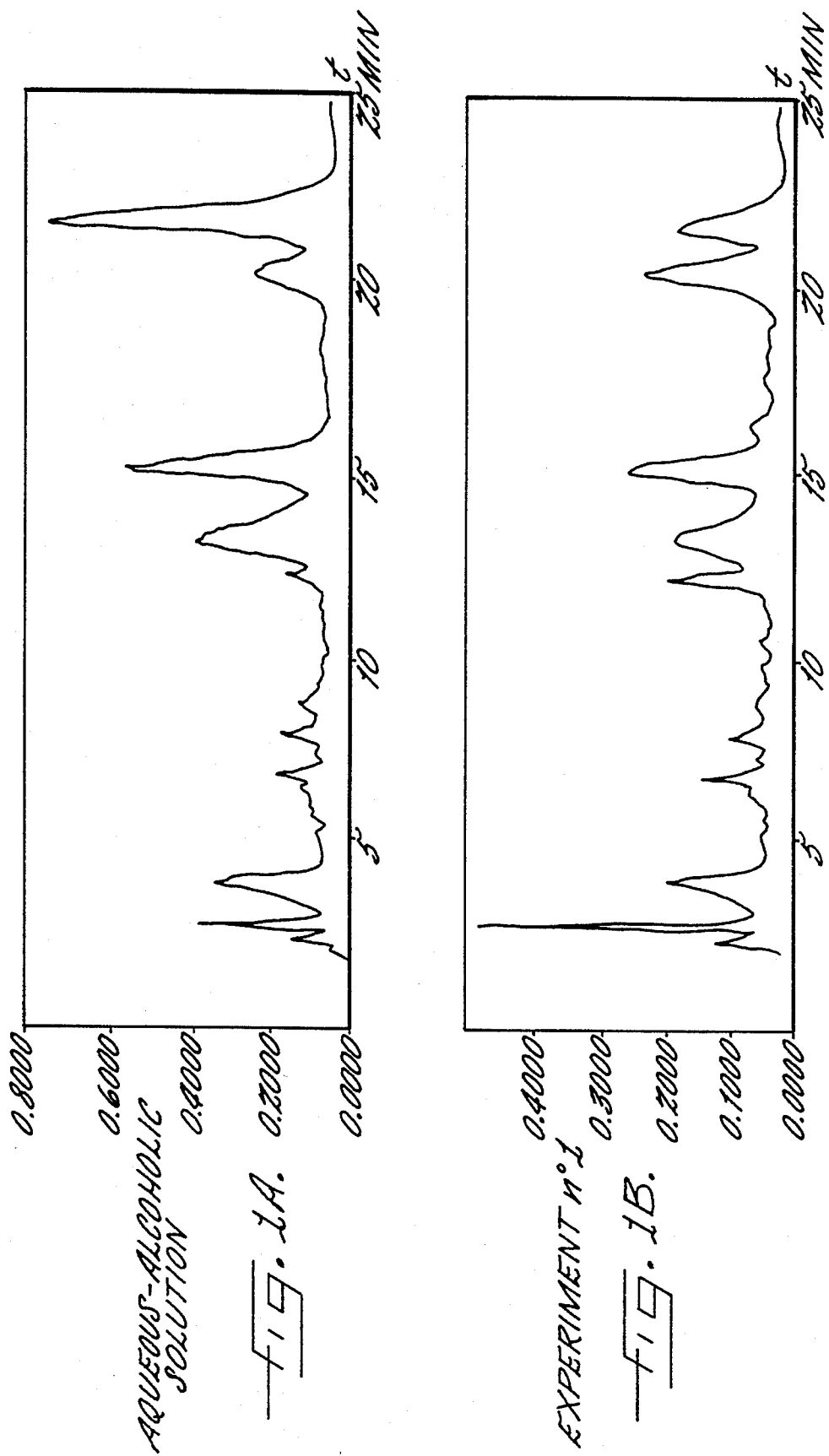

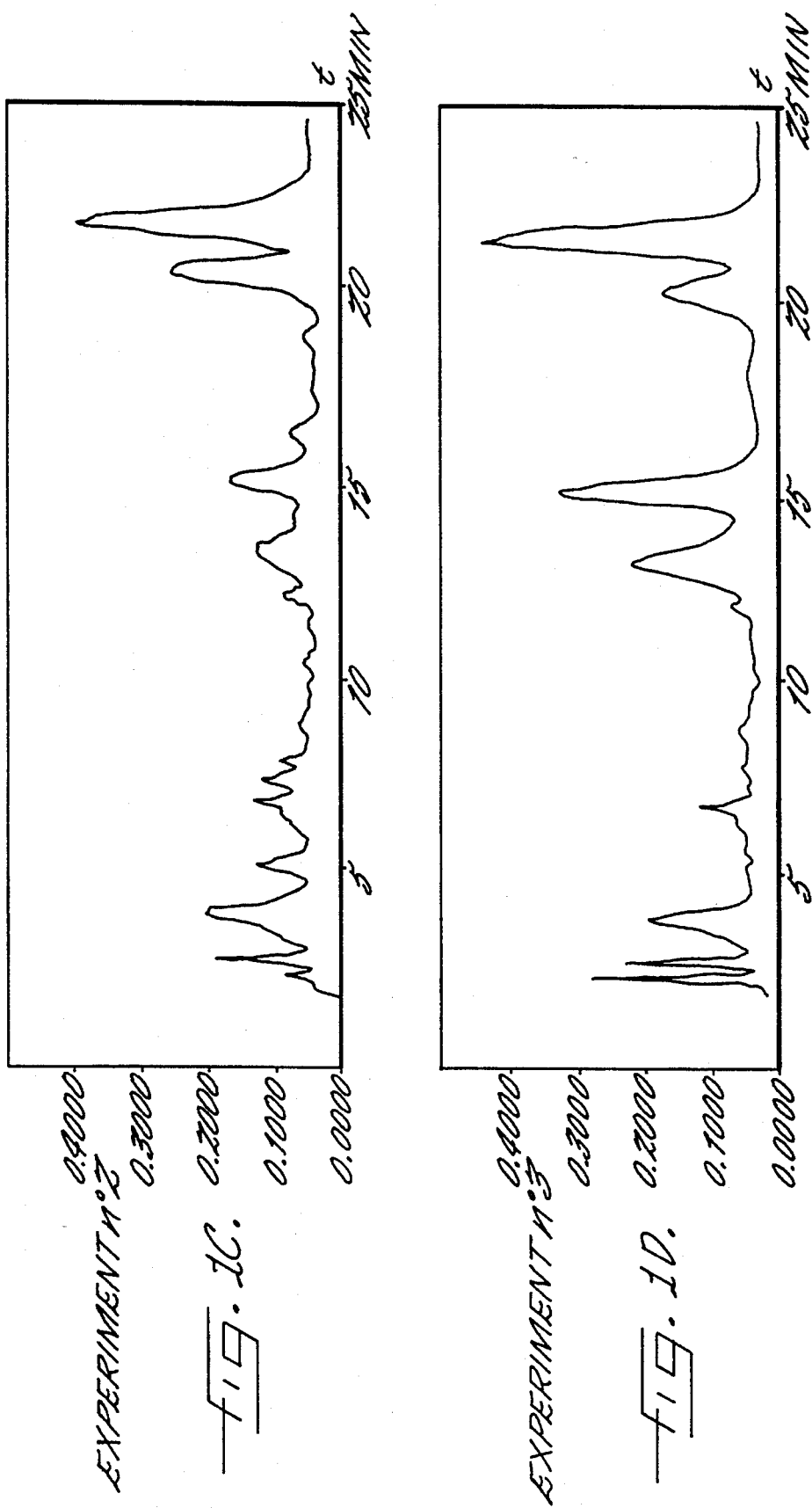

DRY AND POROUS GALENIC FORM BASED ON PLANTS, ITS METHOD OF PREPARATION AND ITS APPLICATIONS

This is a continuation of application Ser. No. 07/990,990 filed on 16 Dec. 1992, now abandoned.

FIELD OF THE INVENTION

The present invention relates to a solid composition based on fresh and/or dry whole plants and/or parts of plants, and/or on extracts, capable of being converted to a dry and porous galenic form (lyophilized or equivalent form) which is undivided or powdered; such a galenic form is particularly suitable for enhancing the stability and absorption of all the active principles of fresh and/or dry whole plants and/or parts of plants, and/or of extracts.

The invention further relates to the method of preparing said composition in the dry form and of said porous galenic form, based on plants.

BACKGROUND OF THE INVENTION

French patents 2 036 890, 2 366 835 and 2 647 343 describe pharmaceutical forms which are characterized in that they dissolve or disintegrate rapidly in an aqueous medium or in saliva.

However, said patents are not appropriate for handling plants or, in particular, for obtaining plant-based compositions in the solid form which have an enhanced absorption and result in a distinctly improved bioavailability of the active principles. In fact, the chemical composition of the active principles of a plant and/or part of a plant is very complex; the basic molecules, namely heteroside genins, terpene and tri-terpene derivatives, alkaloids, phenolic products, various volatile products, etc., are present in association with other molecules, in particular sugars, giving them very different molecular weights ranging from 100–200 to several thousand daltons; these heterosides are very sensitive to degradation, both during the preparation of the composition, due to the different treatments which they can undergo, and during their administration.

European patent application 0 420 729 describes a preparative technique resulting in the stabilization of fresh or dry whole plants and/or parts of plants, or of their extracts, which makes it possible to obtain the totum of the stabilized starting plant material in a form which is stable in a liquid medium, principally an alcoholic medium.

Said European patent application 0 420 729 also describes the preparation of a solid composition by a physical operation or absorption on a support. However, such a solid composition has a number of disadvantages:

the percentage of support must be markedly greater than that of the plant suspension in order effectively to have an absorption capacity, the resulting solid composition contains solvents which are incompatible with conversion of this composition to a porous galenic form (especially lyophilizate), and the plants' active principles of the solid forms described in said patent application do not have an optimal bioavailability.

It was therefore of particular interest to be able to provide a dry galenic form based on plants, which is stable and permits the absorption of all the active principles, without degradation of the latter, especially at the moment of absorption (improvement of the bioavailability).

SUMMARY OF THE INVENTION

Continuing its studies, the Applicant has found that it is possible to obtain a dry and porous galenic form from a solid composition based on plants, which is stable to chemical, enzymatic, bacterial or fungal degradation due to the preparation, and whose absorption by the mucous membranes is significantly enhanced.

The object of the present invention was consequently to provide a composition in the solid form based on whole plants and/or parts of plants, which is capable of being converted to a dry and porous galenic form and which better satisfies practical needs, especially in that it avoids any degradation of the plants' active principles and permits perlingual absorption of all these active principles, thereby also preventing their degradation in the digestive tract.

The present invention relates to a solid composition I based on plants, characterized in that it comprises a mixture of at least:

(A) one or more of the plants' active principles included in a homogeneous suspension of fresh or dry plants obtained by (a) cleaning and/or drying of the plant or part of the plant, (b) cryocomminution at a temperature below 0° C. until a particle size of less than about 100 μm is obtained, (c) immersion of the particles for a suitable time in at least one appropriate solvent, (d) separation of the liquid phase and the solid phase of the suspension obtained, (e) expression of the solid phase obtained in (d) by cold pressing, and (f) mixing of the liquid phase obtained in (d) and the expressed liquid obtained in (e), and (B) at least one absorption promoter with a sequestering action, said mixture (A+B) being dried by removal of the solvent.

In one advantageous embodiment of said composition, the absorption promoter with a sequestering action is selected from α-, β- or γ-cyclodextrins, polymerized cyclodextrins or cyclodextrins substituted for example by methyl, ethyl, hydroxyethyl or hydroxypropyl radicals, aminocyclodextrins and maltodextrins.

In an advantageous arrangement of this embodiment, said composition comprises an association of β-cyclodextrin and maltodextrins as the absorption promoter with a sequestering action.

The solid composition I has the advantage of permitting the immobilization of all the plants' active principles present, irrespective of their structure and their molecular weight, and permits enhanced stabilization of all of said active principles; furthermore, this composition I in the solid form also has the advantage of containing a minimal amount of solvents and of being capable of being converted to a dry and porous galenic form which makes it possible further to enhance the absorption of said plants' active principles by the mucous membranes.

In another advantageous embodiment of said solid composition I based on plants, the amount (by weight) of the active principles relative to the absorption promoter with a sequestering activity varies in proportions ranging from 5 to 50%, preferably between 10 and 25–30% by weight.

In another advantageous embodiment of said composition I, said drying is carried out until the organic solvents have been completely removed and the aqueous solvents have been removed to an extent of the order of 90%.

The solvents can be removed especially by a physical operation such as evaporation, desiccation, atomization or tangential filtration.

Preferably, if said removal is effected by evaporation, this is carried out under reduced pressure and is optionally associated with exposure to ultrahigh frequencies.

The present invention further relates to a solid composition II based on plants, characterized in that it comprises:

a solid composition I such as defined above (dried mixture of (A)+(B)), and (C) at least one absorption promoter selected from surfactants.

In one advantageous embodiment of said composition II, the surfactant-type absorption promoter is selected from glycyrrhizinic acid or one of its salts and sodium glycyrrhetinate.

In another advantageous embodiment of said solid composition II based on plants, the amount of surfactant-type absorption promoter is between 0.5 and 5% (w/w) and preferably of the order of 1% (w/w).

Surprisingly, such a composition II in the solid form, based on plants, is particularly capable of being converted to a dry and porous galenic form (lyophilized or equivalent form) which exhibits enhanced absorption of the plants' active principles by the mucous membranes.

The present invention further relates to a dry and porous galenic form which is undivided or powdered, characterized in that it comprises a lyophilized solid composition II optionally associated with excipients which are suitable from a pharmaceutical point of view.

Surprisingly, such a dry and porous galenic form based on plants exhibits enhanced absorption of the plants' active principles, since it dissolves or disintegrates rapidly in an aqueous medium (especially saliva) and facilitates the passage of all the stabilized original active principles of the plants and/or parts of plants through the mucous membranes (perlingual passage, for example).

BRIEF DESCRIPTION OF THE DRAWINGS

FIG. 1A is an HPLC chromatographic profile of the aqueous-alcoholic solution of willow bark of Example 1, without any absorption promoters.

FIG. 1B is an HPLC chromatographic profile of the aqueous-alcoholic solution of willow bark of Example 1, with the absorption promoters listed in Experiment 1 therein.

FIG. 1C is an HPLC chromatographic profile of the aqueous-alcoholic solution of willow bark of Example 1, with the absorption promoters listed in Experiment 2 therein.

FIG. 1D is an HPLC chromatographic profile of the aqueous-alcoholic solution of willow bark of Example 1, with the absorption promoters listed in Experiment 3 therein.

DETAILED DESCRIPTION OF THE INVENTION

The use of adjuvants or absorption promoters has been mentioned in numerous publications or patents. Cyclodextrins, for example, enhance the absorption of cholecalciferol (DUCHENE et al., *S.T.P. Pharma*, 1(1), 37–43 (1985)) and vitamins A, E and K (DUCHENE D. et al., *Labo Pharma Probl.*, 32(348), 842–850 (1984) and SZEJTLI J. et al., *Die Stärke*, 32(11), 386–391 (1980)); sodium glycyrrhetinate enhances the nasal absorption of insulin (MISHIMA et al., *J. Pharmacobio-Dyn.*, 10, s-69 (1987)); and glycyrrhizinic acid and its salts enhance the absorption of calcitonin through a mucous membrane (French patent no. 2 623 090).

However, the Applicant has found, surprisingly, that the association of a surfactant-type absorption promoter, in particular glycyrrhizinic acid or one of its salts, with an absorption promoter with a sequestering activity (for example β-cyclodextrin) has a synergistic effect on the absorption of the associated active principles by the mucous membranes, and more particularly by the buccal mucous membrane, said synergistic action being further enhanced when said composition is porous (lyophilization).

Advantageously, said dry and porous galenic form based on plants also comprises suitable excipients such as diluents, binders, disintegrating agents and surface-active agents, if appropriate associated with optional additives such as flavourings, perfumes or sweeteners, colours, preservatives or pH correctors.

Such dry and porous galenic forms based on plants have the dual advantage of:

preserving all the plants' active principles in the state in which they occur in the plant and/or part of the plant, and exhibiting markedly improved absorption by the mucous membranes through the association of two different types of absorption promoter and conversion to a porous form (lyophilization in particular), thereby increasing the efficacy of said active principles by virtue of their improved bioavailability.

The diluents which are used more particularly in the dry and porous galenic forms according to the invention are especially pharmaceutically acceptable and preferably soluble substances selected especially from lactose, mannitol, glycocoll, sorbitol or mixtures of these substances.

The binders which are used more particularly in the galenic forms according to the invention are especially any substance which is soluble or dispersible in water, able to ensure the cohesion of said compositions and inert towards the active principles. These substances are preferably selected from polysaccharides such as, for example, natural gums of the gum arabic type, alginates, pectins, gelatin, synthetic gums of the xanthan gum type, dextrans, dextrin, cellulose derivatives, polyvinyl alcohol, polyvinylpyrrolidone or else mixtures of these substances.

The disintegrating agents, surface-active agents, flavourings, perfumes or sweeteners, colours, preservatives and pH correctors are those normally used in the pharmaceutical and food industry for the preparation of comparable forms and compatible with the active principles present.

The present invention further relates to a method of preparing the dry and porous galenic form according to the invention, characterized in that it comprises the following steps:

1) preparation of a homogeneous suspension (A) of plants containing one or more active principles by (a) cleaning and/or drying of the plant or part of the plant, (b) cryocomminution at a temperature below 0° C. until a particle size of less than about 100 μm is obtained, (c) immersion of the particles for a suitable time in at least one appropriate solvent, (d) separation of the liquid phase and the solid phase of the suspension obtained, (e) expression of the solid phase obtained in (d) by cold pressing, and (f) mixing of the liquid phase obtained in (d) and the expressed liquid obtained in (e);

2) immobilization of the plants' active principles obtained in 1) by mixing the suspension (A) with at least one absorption promoter with a sequestering activity, (B);

3) removal of the solvents contained in the mixture obtained in 2) to give a composition I according to the invention;

4) preparation of a paste from a composition II according to the invention by mixing the product obtained in 3) (composition I) with a preparation containing at least one surfactant-type absorption promoter (C), if appropriate associated with optional diluents, binders and additives, together with a suitable amount of liquid; and 5) conversion of the composition obtained in 4) to a porous form, especially by freezing and sublimation (lyophilization) or an equivalent operation.

In one advantageous mode of carrying out said method, said removal comprises the complete removal of the organic solvents and the removal of the aqueous solvents to an extent of the order of 90%.

In another mode of carrying out the method, the removal of the solvents is preceded by a concentration process, for example by osmosis.

Preferably, the plants' active principles obtained in an aqueous-alcoholic medium according to European patent application 0 420 729 are immobilized by addition of the absorption promoter(s) with a sequestering activity (coprecipitation).

In another advantageous mode of carrying out said method, the amount (by weight) of the active principles relative to the absorption promoters with a sequestering activity varies in proportions ranging from 5 to 50%, preferably between 10 and 25–30% by weight.

In another advantageous mode of carrying out said method, the amount of surfactant-type absorption promoter is between 0.5 and 5% (w/w) and preferably of the order of 1% (w/w).

The dry and porous galenic forms according to the invention are applicable in the pharmaceutical, veterinary, dietetic, food or cosmetic sector.

Apart from the foregoing provisions, the invention also includes other provisions which will become apparent from the following description referring to Examples of compositions and of how to carry out the method, forming the subjects of the present invention.

It must be clearly understood, however, that these Examples are given solely in order to illustrate the subject of the invention without in any way implying a limitation.

EXAMPLE 1:

The following three preparations, derived from one and the same aqueous-alcoholic solution of willow (bark) obtained according to European patent application 0 420 729, were made up in a planetary mixer capable of withstanding a reduced pressure and equipped with an ultra-high frequency generator:

|  | EXPERIMENT 1 | EXPERIMENT 2 | EXPERIMENT 3 |
| --- | --- | --- | --- |
| willow, equivalent in terms of dry plant to | 50 g | 50 g | 50 g |
| β-cyclodextrin | 25 g | — | 15 g |
| maltodextrins | — | 25 g | 10 g |
| residual water content | 6.3% | 2.5% | 4.1% |

A chromatographic study by HPLC was carried out; if the profiles obtained with the three experiments (FIG. 1) are compared with that of the starting aqueous-alcoholic solution, it is seen that all the components of the willow have been stabilized by the mixture of absorption promoters with a sequestering activity.

EXAMPLE 2:

A preparation, derived from an aqueous-alcoholic solution of burdock roots prepared according to Example 1 of European patent application 0 420 729, the composition of which is shown in the Table below, was made up as described in Example 1 above:

| COMPONENT | EXPERIMENT |
| --- | --- |
| burdock, equivalent in terms of dry plant to | 50 g |
| β-cyclodextrin | 15 g |
| maltodextrins | 10 g |
| residual water content | 5.8% |

An analytical study of the aqueous-alcoholic solution and the preparation described above was carried out. The results are expressed on the basis of the equivalent in terms of dried roots, as shown in the Table below.

|  | SOLUTION | PREPARATION |
| --- | --- | --- |
| PROTEINS |  |  |
| total | 1.8% | 1.8% |
| free amino acids | 0.3% | 0.4% |
| amino acids after hydrolysis | 1.4% | 1.4% |
| SUGARS |  |  |
| total | 10.5% | 11.6% |
| inulin | 10% | 11% |
| glucose | 0.180% | 0.180% |
| sucrose | 0.180% | 0.170% |
| MISCELLANEOUS |  |  |
| lipids | traces | traces |
| vitamin E | 0.000015% | 0.000014% |
| flavonoids | 0.09% | 0.12% |
| sterols | 0.0009% | 0.0010% |
| tannins | presence | presence |
| saponins | presence | presence |

There is a strong similarity between the two analyses.

EXAMPLE 3:

An aqueous-alcoholic solution of willow (bark) and the absorption promoters with a sequestering activity, β-cyclodextrin and maltodextrins, are introduced into a planetary mixer capable of withstanding a reduced pressure and equipped with an ultra-high frequency generator. The ingredients are mixed for 1 hour and part of the solvent is then removed under vacuum by means of microwaves (discontinuous excitation) without exceeding 35° C. The operation is stopped when the amount of solvent is about 0.6 g per unit. All the other excipients according to the following composition (unit formula) are then introduced:

| aqueous-alcoholic solution of willow, equivalent in terms of dry plant to | 500 mg |
| --- | --- |
| β-cyclodextrin | 285 mg |
| maltodextrins | 150 mg |
| lactose | 920 mg |
| gum arabic | 33 mg |
| ammonium glycyrrhizinate* | 15 mg |
| aspartame | 11 mg |

*surfactant-type absorption promoter

The ingredients are mixed for 1 hour and 1.5 g oral lyophilizates are prepared in conventional manner. The disintegration time varies from 2 to 4 minutes.

EXAMPLE 4:

A preparation made up as described above in Example 3, containing β-cyclodextrin and ammonium glycyrrhizinate as absorption promoters, respectively with a sequestering activity and of the surfactant type, is compared with the following preparations in an experiment on absorption by the mucous membranes of the buccal cavity:

|  | EXPERIMENT 1 (subject of the invention) | EXPERIMENT 2 | EXPERIMENT 3 | EXPERIMENT 4 |
| --- | --- | --- | --- | --- |
| solution of nettle root (β-sitosterol content) | 5.2 mg | 5.2 mg | 5.2 mg | 5.2 mg |
| β-cyclodextrin | 285 mg | 285 mg | — | — |
| maltodextrins | 150 mg | 150 mg | 150 mg | 150 mg |
| ammonium glycyrrhizinate | 15 mg | — | 15 mg | — |
| gum arabic | 33 mg | 33 mg | 33 mg | 33 mg |
| lactose | 920 mg | 935 mg | 1205 mg | 1220 mg |
| aspartame | 11 mg | 11 mg | 11 mg | 11 mg |

The absorption is determined by the buccal absorption test described by BECKETT A. H. and TRIGGS E. J., J. Pharm. Pharmacol., 19, 318–418, 1967. Two oral lyophilizates, i.e. the equivalent of 10.4 mg of β-sitosterol, are given to six volunteers. The level of β-sitosterol absorbed by the mucous membranes is determined by GC.

The results are shown in the following Table:

|  | Dose administered in mg | Level absorbed in mg |
| --- | --- | --- |
| EXPERIMENT 1 | 10.4 mg | 8.9 mg |
| EXPERIMENT 2 | 10.4 mg | 4.6 mg |
| EXPERIMENT 3 | 10.4 mg | 5.8 mg |
| EXPERIMENT 4 | 10.4 mg | 1.8 mg |

Experiment 1, which corresponds to the administration of a composition according to the invention, shows a markedly improved absorption relative to the other experiments.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

That which is claimed is:

1. A dry and porous galenic composition consisting essentially of:

(A) the active agents of a plant in a homogeneous suspension of plant material obtained by (a) cryocomminuting said plant at a temperature below 0° C. until particles of less than about 100 μm are obtained; (b) immersing said particles in an appropriate solvent to obtain a suspension; (c) separating the liquid phase and the solid phase of the suspension obtained in step (b); (d) expressing the solid phase obtained in step (c) by cold pressing; and (e) mixing the liquid phase obtained in (c) and the c ..pressed liquid obtained in (d);

(B) at least one absorption promoter with a sequestering action, said absorption promoter being selected from the group consisting of α cyclodextrins; β cyclodextrins; γ-cyclodextrins; polymerized cyclodextrins; dextrins substituted by methyl, ethyl, hydroxyethyl or hydroxypropyl radicals; aminocyclodextrins and maltodextrins; and (C) a surfactant-type absorption promoter selected from the group consisting of glycyrrhizinic acid, salts of glycyrrhizinic acid, and sodium glycyrrhetinate;

wherein the components (A) and (B) are combined and dried until organic solvents are essentially completely removed and about 90% of aqueous solvents are removed, prior to step (C);

wherein the amount by weight of said active agents relative to said absorption promoter with a sequestering activity is from 5% to 50%, and the amount by weight of said surfactant-type absorption promoter relative to said combination of components (A) and (B) is between 0.5 and 5%;

wherein said surfactant-type absorption promoter is added simultaneously with a suitable amount of liquid to form a paste; and wherein said paste is converted to a porous form, by freezing and sublimation.

2. A dry and porous galenic composition according to claim 1, wherein said plant is a fresh plant.

3. A dry and porous galenic composition according to claim 1, wherein said plant is a dried plant.

4. A dry and porous galenic composition according to claim 1, wherein the amount of active agents relative to said absorption promoter with a sequestering activity varies in a range from about 10% to about 30% by weight.

5. A dry and porous galenic composition according to claim 1, wherein the amount of surfactant-type absorption promoter is about 1% by weight.

6. A dry and porous galenic composition according to claim 1, wherein said composition is powdered.

7. A dry and porous galenic composition according to claim 1, wherein said composition is in lyophilized form.

8. A dry and porous galenic composition according to claim 1, further comprising pharmaceutically acceptable excipients.

9. A dry and porous galenic composition according to claim 1, wherein said absorption promoter with a sequestering activity comprises β-cyclodextrin and maltodextrins.

10. A method of preparing a dry and porous galenic composition, consisting of the following steps:

(1) preparing a homogenous suspension of a plant containing active agents by (a) cryocomminuting said plant at a temperature below 0° C. until a particle size of less than about 100 μm is obtained, (b) immersing the particles in an appropriate solvent to obtain a suspension, (c) separating the liquid phase and the solid phase of the suspension obtained in step (b), (d) expressing the solid phase obtained in step (c) by cold pressing, and (e) mixing the liquid phase obtained in step (c) and the expressed liquid obtained in step (d);

(2) immobilizing the plants' active agent obtained in step (1) by mixing the suspension with at least one absorption promoter having a sequestering activity selected from the group consisting of α, β and γ-cyclodextrins, polymerized cyclodextrins, dextrins substituted by methyl, ethyl, hydroxyethyl or hydroxypropyl radicals, aminocyclodextrins and maltodextrins, and wherein the amount by weight of the active agents relative to said absorption promoter with a sequestering activity is between 5 and 50%;

(3) removing essentially all organic solvents and about 90% of the aqueous solvents contained in the mixture obtained in step (2) to give a solid composition;

(4) mixing the product obtained in step (3) with at least one surfactant-type absorption promoter selected from the group consisting of glycyrrhizinic acid, salts of glycyrrhizinic acid, and sodium glycyrrhetinate, and a suitable amount of liquid to form a paste, wherein the amount by weight of said surfactant-type absorption promoter relative to said composition obtained in step (3) is between 0.5 and 5%; and (5) converting the composition obtained in step (4) to a porous form by freezing and sublimation.

11. A method according to claim 10, wherein the removal of the solvents is preceded by a concentration process.

12. A method according to claim 10, wherein the amount of active agents relative to said absorption promoter with a sequestering activity varies in a range from about 10% to about 30% by weight.

13. A method according to claim 10, wherein the amount of surfactant-type absorption promoter is about 1% by weight.

14. A method according to claim 10, further comprising the step of adding pharmaceutically acceptable excipients.

15. A method of improving the absorption of active agents through mucosal membranes, comprising the administration of an absorption-improving amount of a dry and porous galenic composition according to claim 1.

* * * * *